(12) United States Patent
Mou et al.

(10) Patent No.: US 11,885,727 B2
(45) Date of Patent: Jan. 30, 2024

(54) HOME DEVICE CAPABLE OF GAS DETECTION

(71) Applicant: Microjet Technology Co., Ltd., Hsinchu (TW)

(72) Inventors: Hao-Jan Mou, Hsinchu (TW); Yung-Lung Han, Hsinchu (TW); Chi-Feng Huang, Hsinchu (TW); Chun-Yi Kuo, Hsinchu (TW); Yi-Ting Lu, Hsinchu (TW); Chang-Yen Tsai, Hsinchu (TW); Wei-Ming Lee, Hsinchu (TW)

(73) Assignee: MICROJET TECHNOLOGY CO., LTD., Hsinchu (TW)

( * ) Notice: Subject to any disclaimer, the term of this patent is extended or adjusted under 35 U.S.C. 154(b) by 87 days.

(21) Appl. No.: 17/133,945

(22) Filed: Dec. 24, 2020

(65) Prior Publication Data

US 2021/0208049 A1 Jul. 8, 2021

(30) Foreign Application Priority Data

Jan. 8, 2020 (TW) ................................. 109100667

(51) Int. Cl.
*G01N 15/06* (2006.01)
*G01N 15/02* (2006.01)
*G01N 1/24* (2006.01)

(52) U.S. Cl.
CPC .............. *G01N 15/06* (2013.01); *G01N 1/24* (2013.01); *G01N 15/0205* (2013.01); *G01N 2015/0693* (2013.01)

(58) Field of Classification Search
CPC ............. G01N 1/2273; G01N 33/0031; G01N 33/0009; G01N 33/004; G01N 33/0022; G01N 33/0047; G01N 33/0073; G01N 33/0062; G01N 15/06; G01N 2015/0046; G01N 27/407; G01N 1/24; G01N 15/0211; G01N 15/0656; G01N 15/1459; G01N 27/4045; G01N 33/0039;
(Continued)

(56) References Cited

U.S. PATENT DOCUMENTS 10,935,478 B2 * 3/2021 Mou ................... G01N 15/0656
2019/0011336 A1 * 1/2019 Mou ..................... G01N 33/004
(Continued)

FOREIGN PATENT DOCUMENTS

CN 107623801 A 1/2018
CN 209432182 U 9/2019
(Continued)

*Primary Examiner* — Harshad R Patel
*Assistant Examiner* — Gedeon M Kidanu
(74) *Attorney, Agent, or Firm* — Birch, Stewart, Kolasch & Birch, LLP

(57) ABSTRACT

The home device capable of gas detection is provided and includes a main body and a gas detection module. The main body has at least one inlet, at least one outlet and a gas flowing channel disposed between the at least one inlet and the at least one outlet. The gas detection module is disposed in the gas flowing channel of the main body and includes a piezoelectric actuator and at least one sensor. Gas is inhaled into the gas flowing channel through the inlet by the piezoelectric actuator, is discharged out through the outlet, and is transported to the at least one sensor to be detected so as to obtain gas information.

20 Claims, 19 Drawing Sheets

(58) Field of Classification Search
CPC ... G01N 2001/2276; G01N 2015/0693; G01N 2015/1486; G01N 33/0037; G01N 33/0063; G01N 33/0075; G01N 33/497; G01N 1/10; G01N 1/14; G01N 1/22; G01N 1/44; G01N 15/02; G01N 15/0205; G01N 15/0606; G01N 15/0637; G01N 15/1404; G01N 2015/0007; G01N 2015/0019; G01N 2015/1493; G01N 2033/0068; G01N 2035/00455; G01N 27/4074; G01N 33/0004; G01N 33/0011; G01N 33/0013; G01N 33/0014; G01N 33/0027; G01N 33/0032; G01N 33/0036; G01N 33/0042; G01N 33/0067; G01N 33/007; G08B 21/12; G08B 21/14; G08B 27/005; G08B 27/006

See application file for complete search history.

(56) References Cited

U.S. PATENT DOCUMENTS

| | | | | |
|---|---|---|---|---|
| 2019/0011390 A1* | 1/2019 | Mou | | G01N 33/0022 |
| 2019/0011391 A1* | 1/2019 | Mou | | F04B 19/006 |
| 2019/0011392 A1* | 1/2019 | Mou | | F04B 43/046 |
| 2019/0011394 A1* | 1/2019 | Mou | | G01N 1/2273 |
| 2019/0011949 A1* | 1/2019 | Mou | | G06F 1/1688 |
| 2019/0033177 A1* | 1/2019 | Mou | | F04B 43/046 |
| 2019/0033278 A1* | 1/2019 | Mou | | G08B 21/12 |
| 2019/0033280 A1* | 1/2019 | Mou | | G08B 21/12 |
| 2019/0046914 A1* | 2/2019 | Mou | | B01D 46/442 |
| 2019/0056125 A1* | 2/2019 | Mou | | F24F 3/16 |
| 2019/0056292 A1* | 2/2019 | Mou | | F04B 45/047 |
| 2019/0056367 A1* | 2/2019 | Mou | | H05K 5/065 |
| 2019/0056368 A1* | 2/2019 | Mou | | G08B 21/12 |
| 2019/0056369 A1* | 2/2019 | Mou | | G01N 33/007 |
| 2019/0056766 A1* | 2/2019 | Mou | | G06F 1/1601 |
| 2019/0060682 A1* | 2/2019 | Mou | | A62B 23/025 |
| 2019/0064104 A1* | 2/2019 | Mou | | F15B 15/20 |
| 2019/0067553 A1* | 2/2019 | Mou | | H01L 41/0471 |
| 2019/0170717 A1* | 6/2019 | Mou | | G01N 33/0031 |
| 2019/0200897 A1* | 7/2019 | Mou | | A61B 5/082 |
| 2019/0212242 A1* | 7/2019 | Mou | | G01N 15/06 |
| 2019/0265132 A1* | 8/2019 | Mou | | G01N 33/0009 |
| 2019/0302072 A1* | 10/2019 | Mou | | G01N 33/004 |
| 2019/0302073 A1* | 10/2019 | Mou | | H04M 1/035 |
| 2019/0331564 A1* | 10/2019 | Mou | | G01N 33/0014 |
| 2019/0331582 A1* | 10/2019 | Mou | | G01N 15/0637 |
| 2019/0376877 A1* | 12/2019 | Mou | | G01N 1/14 |

FOREIGN PATENT DOCUMENTS

| | | |
|---|---|---|
| JP | 2013-127681 A | 6/2013 |
| TW | M581748 U | 8/2019 |

* cited by examiner

HOME DEVICE CAPABLE OF GAS DETECTION

FIELD OF THE INVENTION

The present disclosure relates to a home device capable of gas detection, and more particularly to a home device capable of gas detection to provide gas information.

BACKGROUND OF THE INVENTION

Due to the increasing air pollution recently, people pay more and more attention to the quality of the air around their lives. For example, carbon monoxide, carbon dioxide, volatile organic compounds (VOC), PM2.5, nitric oxide, sulfur monoxide and even the suspended particles contained in the air are exposed in the environment and affected the human health, and even endanger the life seriously. Therefore, the quality of environmental air has attracted the attention in various countries. At present, how to detect the air quality and away from harmful environment is a problem that urgently needs to be solved.

In order to confirm the quality of the air, it is feasible to use a gas sensor to detect the air in the surrounding environment. If the detection information can be provided in real time to warn the people in this environment, it would be helpful of avoiding the harm stem therefrom and facilitates the people to escape from the hazard environment immediately, and prevents human health from affecting by the hazardous gas exposed in the environment and causing harmful result. Therefore, it is a very excellent application to use a gas sensor to detect the air in the surrounding environment. It becomes an important improvement to combine a home device and an air quality detection device and allow the users to monitor the air quality in the house in real time in the present disclosure.

SUMMARY OF THE INVENTION

An object of the present disclosure is to provide a home device capable of gas detection. By combining the gas detection module with the home device, the air quality surrounding the user can be detected by the gas detection module in real time at any moment.

In accordance with an aspect of the present disclosure, a home device capable of gas detection including a main body and a gas detection module is provided. The main body has at least one inlet, at least one outlet and a gas flowing channel disposed between the at least one inlet and the at least one outlet. The gas detection module is disposed in the gas flowing channel of the main body and includes a piezoelectric actuator and at least one sensor. Gas is inhaled into the gas flowing channel through the inlet by the piezoelectric actuator, discharged out through the outlet, and transported to the at least one sensor to be detected so as to obtain gas information.

The above contents of the present disclosure will become more readily apparent to those ordinarily skilled in the art after reviewing the following detailed description and accompanying drawings, in which:

DETAILED DESCRIPTION OF THE PREFERRED EMBODIMENT

The present disclosure will now be described more specifically with reference to the following embodiments. It is to be noted that the following descriptions of preferred embodiments of this invention are presented herein for purpose of illustration and description only. It is not intended to be exhaustive or to be limited to the precise form disclosed.

Figure 1:
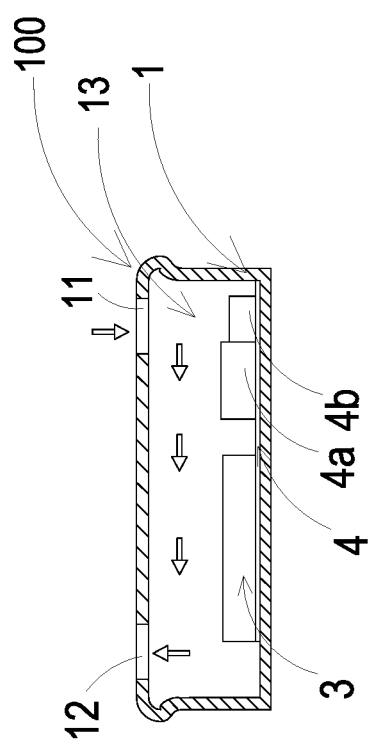
FIG. 1 shows a schematic cross-sectional view illustrating a home device capable of gas detection according to an embodiment of the present disclosure.

Please refer to FIG. 1. The present disclosure provides a home device 100 having gas detection function. In an embodiment, the home device 100 is a video and audio output device and is one selected from a group consisting of a player, a radio, a robot, a stereo, a clock, a wall clock, walkie-talkies, a printer, a projector, a Bluetooth speaker and a smart speaker. In an embodiment, the home device 100 is an environmental electrical appliance and is one selected from a group consisting of an air purifier, an air cleaner, a humidifier, a plant detector, an air detector, an air conditioner socket, an electric heater, an air conditioner, a fan, a temperature controller, a dehumidifier and an anion air purifier. In an embodiment, the home device 100 is a household appliance and is one selected from a group consisting of a toilet, a washing machine, a mosquito killer lamp, a sweeping robot, a water heater, a drying rack, a floor mopping machine, a water dispenser, a smart electric lift table, an electric blanket, a vacuum cleaner, a clothes dryer machine, a towel heater rack, a temperature and humidity measuring device and an automatic temperature controller. In an embodiment, the home device 100 is a kitchen appliance and is one selected from a group consisting of a refrigerator, a microwave oven, an electric kettle, a water purifier, a coffee machine, a milk frother, an electric cooker, a range hood, an induction cooker, a pressure cooker, a dishwasher, a juicer, a steaming oven, a sink, a hard water softener, a smoke sensor, a gas sensor and a water sensor. In an embodiment, the home device 100 is a home security device and is one selected from a group consisting of a door lock, a video doorbell, a safe and a window opener. In an embodiment, the home device 100 is a lighting device and is one selected from a group consisting of a ceiling lamp, a bedside lamp, a table lamp, a light bulb and a fan lamp. In an embodiment, the home device 100 is a power conversion device and is one selected from a group consisting of a socket, a power strip and a switch. In an embodiment, the home device 100 is a camera security equipment and is one selected from a group consisting of a camera and a camcorder. In an embodiment, the home device 100 is a wearable device and is one selected from a group consisting of a smart mask, a smart clothing, a smart textile, a smart belt, a smart necklace, a smart brooch and a bracelet. In an embodiment, the home device 100 is a baby product and is one selected from a group consisting of a baby monitor, a stroller and a crib.

The home device 100 includes a main body 1 and a gas detection module 3. The main body 1 includes at least one inlet 11, at least one outlet 12 and a gas flowing channel 13. In this embodiment, the main body 1 has an inlet 11 and an outlet 12, but not limited thereto. The gas flowing channel 13 is disposed between the inlet 11 and the outlet 12. The gas detection module 3 is disposed in the gas flowing channel 13 to detect the gas within the gas flowing channel 13 and obtain gas information.

Please refer to FIGS. 2A to 2C, 3A, 3B, 4, 5A and 5B. The gas detection module 3 includes a base 31, a piezoelectric actuator 32, a driving circuit board 33, a laser component 34, a particulate sensor 35 and an outer cover 36. In the embodiment, the base 31 includes a first surface 311, a second surface 312, a laser loading region 313, a gas-inlet groove 314, a gas-guiding-component loading region 315 and a gas-outlet groove 316. The first surface 311 and the second surface 312 are two opposite surfaces. The laser loading region 313 is hollowed out from the first surface 311 to the second surface 312. The gas-inlet groove 314 is concavely formed from the second surface 312 and disposed adjacent to the laser loading region 313. The gas-inlet groove 314 includes a gas-inlet 314a and two lateral walls. The gas-inlet 314a is in fluid communication with an environment outside the base 31 and is spatially corresponding to the inlet opening 361a of the outer cover 36. The two lateral walls are disposed adjacent to the laser loading region 313 and are penetrated by the transparent window 314b. The transparent window 314b is opened on the lateral wall and is in communication with the laser loading region 313. In that, the first surface 311 of the base 31 is attached and covered with the outer cover 36, and the second surface 312 of the base 31 is attached and covered with the driving circuit board 33, so that an inlet path is defined by the gas-inlet groove 314.

In the embodiment, the gas-guiding-component loading region 315 is concavely formed from the second surface 312 and in fluid communication with the gas-inlet groove 314. A ventilation hole 315a penetrates a bottom surface of the gas-guiding-component loading region 315. The gas-outlet groove 316 includes a gas-outlet 316a, and the gas-outlet 316a is spatially corresponding to the outlet opening 361b of the outer cover 36. The gas-outlet groove 316 includes a first section 316b and a second section 316c. The first section 316b hollowed out from the first surface 311 is spatially corresponding to a vertical projection area of the gas-guiding-component loading region 315. The second section 316c is hollowed out from the first surface 311 to the second surface 312 in a region where the first surface 311 is not aligned with the vertical projection area of the gas-guiding-component loading region 315. The first section 316b and the second section 316c are connected to form a stepped structure. Moreover, the first section 316b of the gas-outlet groove 316 is in fluid communication with the ventilation hole 315a of the gas-guiding-component loading region 315, and the second section 316c of the gas-outlet groove 316 is in fluid communication with the gas-outlet 316a. In that, when the first surface 311 of the base 31 is attached and covered with the outer cover 36, and the second surface 312 of the base 31 is attached and covered with the driving circuit board 33, an outlet path is defined by the gas-outlet groove 316.

Figure 4:
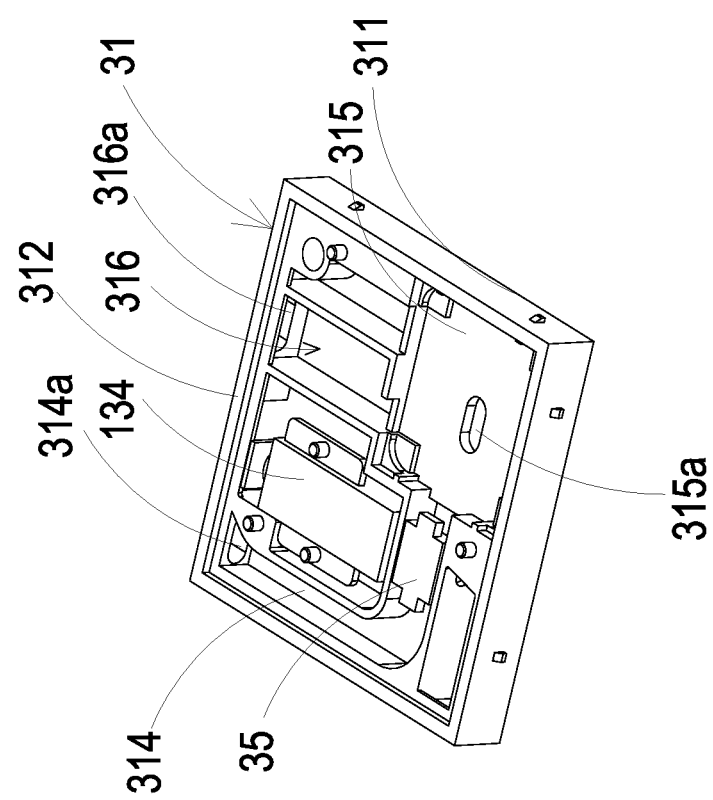
FIG. 4 is a schematic perspective view illustrating a laser component and a particulate sensor accommodated in the base of the present disclosure.

Please refer to FIG. 4. In the embodiment, the laser component 34 and the particulate sensor 35 are disposed on the driving circuit board 33 and accommodated in the base 31. In order to describe the positions of the laser component 34 and the particulate sensor 35 relative to the base 31, the driving circuit board 33 is omitted in FIG. 4 for clarity. Please refer to FIG. 4. The laser component 34 is accommodated in the laser loading region 313 of the base 31, and the particulate sensor 35 is accommodated in the gas-inlet groove 314 of the base 31 and aligned to the laser component 34. In addition, the laser component 34 is spatially corresponding to the transparent window 314b, a light beam emitted by the laser component 34 passes through the transparent window 314b and is irradiated into the gas-inlet groove 314. A light beam path emitted from the laser component 34 passes through the transparent window 314b and extends in a direction perpendicular to the gas-inlet groove 314.

In the embodiment, a projecting light beam emitted from the laser component 34 passes through the transparent window 314b and enters the gas-inlet groove 314, and suspended particles contained in the gas passing through the gas-inlet groove 314 is irradiated by the projecting light beam. When the suspended particles contained in the gas are irradiated to generate scattered light spots, the scattered light spots are detected and calculated by the particulate sensor 35 for obtaining related information in regard to the sizes and the concentration of the suspended particles contained in the gas. In the embodiment, the particulate sensor 35 is a PM2.5 sensor.

Figure 5A:
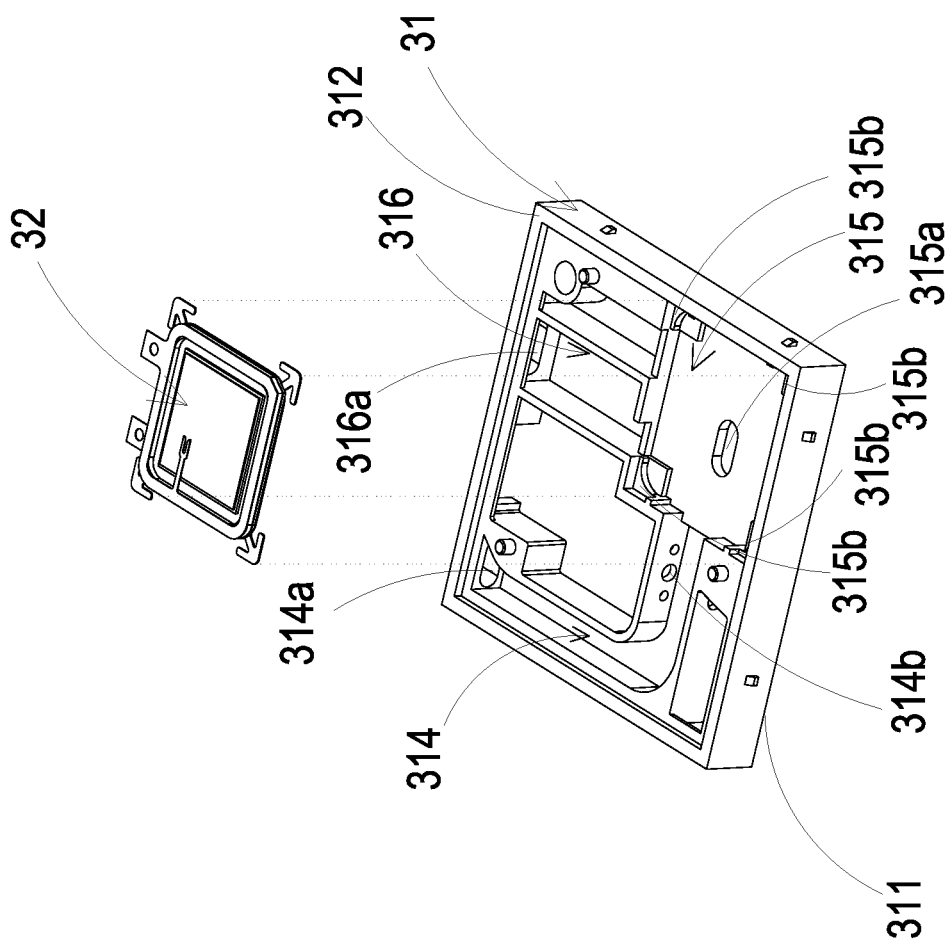
FIG. 5A is a schematic exploded view illustrating the combination of the piezoelectric actuator and the base.
Figure 5B:
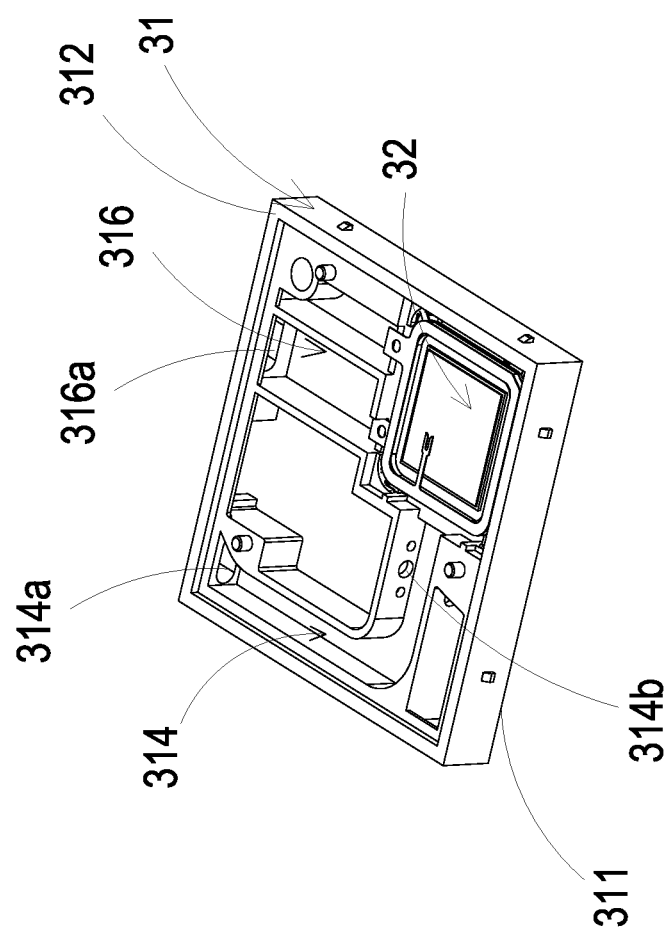
FIG. 5B is a schematic perspective view illustrating the combination of the piezoelectric actuator and the base.

Please refer to FIG. 5A and FIG. 5B. The piezoelectric actuator 32 is accommodated in the gas-guiding-component loading region 315 of the base 31. Preferably but not exclusively, the gas-guiding-component loading region 315 is square and includes four positioning notches 315b disposed at four corners of the gas-guiding-component loading region 315, respectively. The piezoelectric actuator 32 is disposed in the gas-guiding-component loading region 315 through the four positioning notches 315b. In addition, the gas-guiding-component loading region 315 is in fluid communication with the gas-inlet groove 314. When the piezoelectric actuator 32 is enabled, the gas in the gas-inlet groove 314 is inhaled by the piezoelectric actuator 32, so that the gas flows into the piezoelectric actuator 32. Thereafter, the gas is transported into the gas-outlet groove 316 through the ventilation hole 315a of the gas-guiding-component loading region 315. Moreover, through the actions of the piezoelectric actuator 32, the gas outside the main body 1 is inhaled into the gas flowing channel 13 through the inlet 11, flowed through the gas detection module 3 in the gas flowing channel 13, and finally discharged out through the outlet 12, thereby guiding the air to the particulate sensor 35 to be detected and obtain gas information.

Figure 2A:
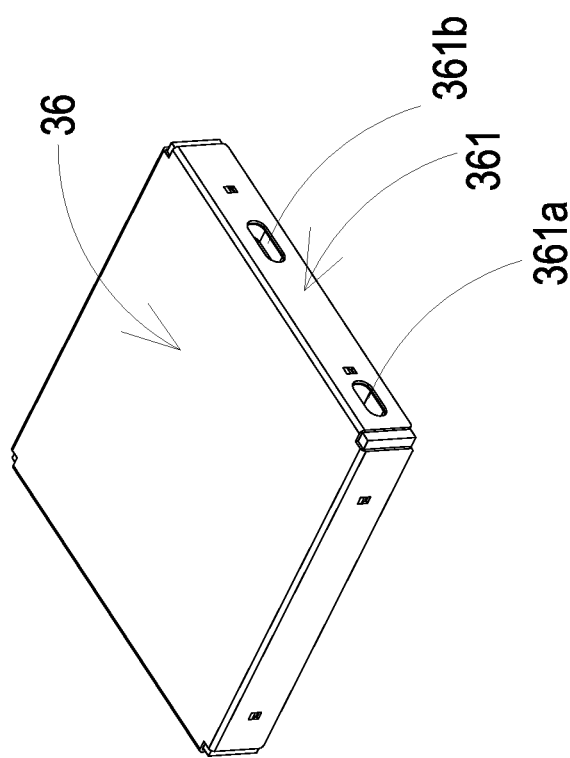
FIG. 2A is a schematic exterior view illustrating a gas detection module according to an embodiment of the present disclosure.
Figure 2B:
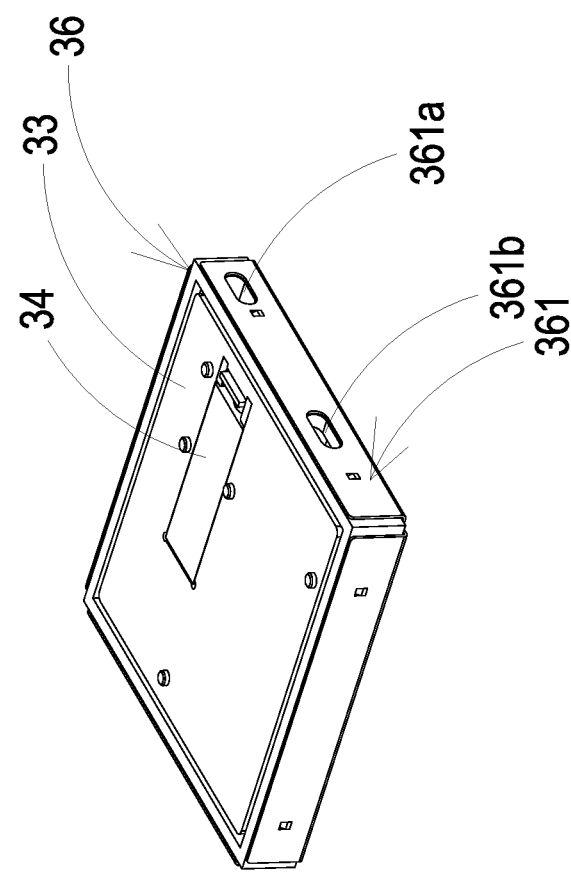
FIG. 2B is a schematic exterior view illustrating the gas detection module according to the embodiment of the present disclosure from another perspective angle.
Figure 2C:
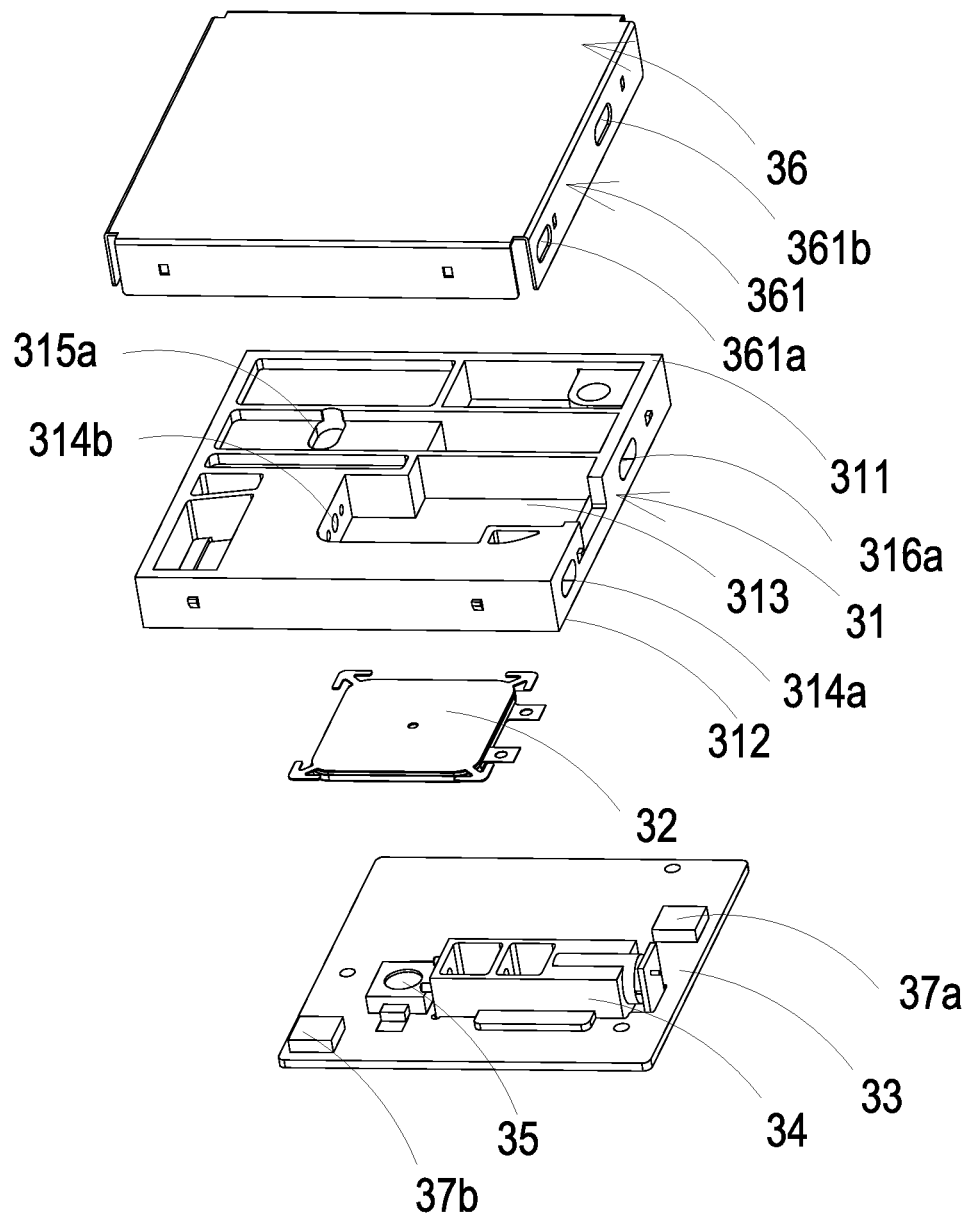
FIG. 2C is a schematic exploded view illustrating the gas detection module of the present disclosure.
Figure 3A:
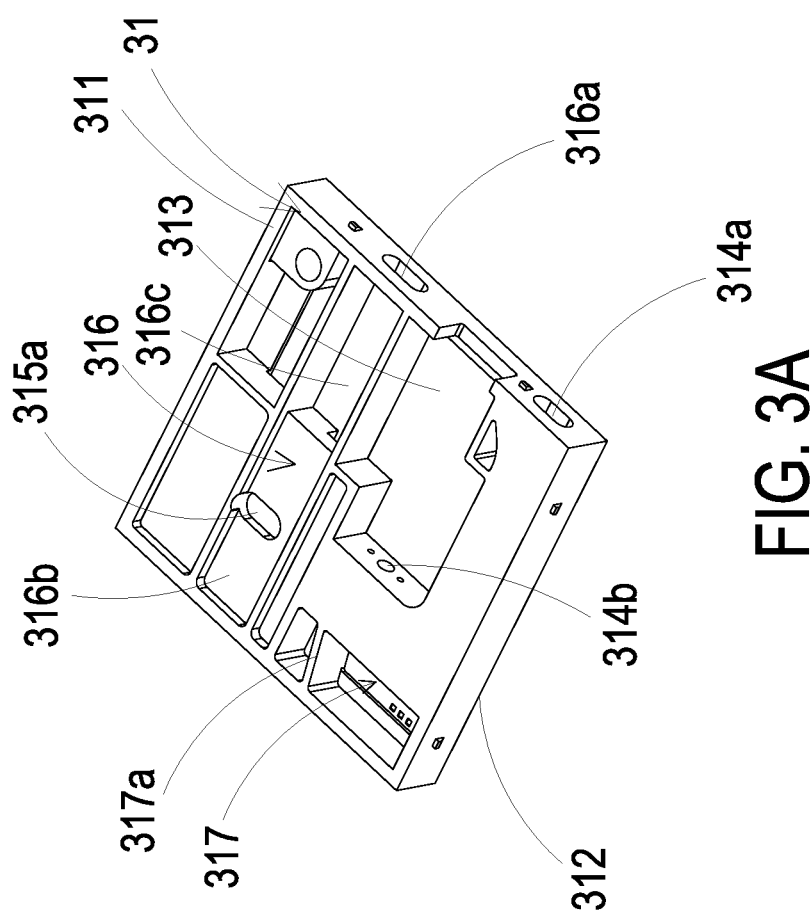
FIG. 3A is a schematic perspective view illustrating a base of the gas detection module of the present disclosure.
Figure 3B:
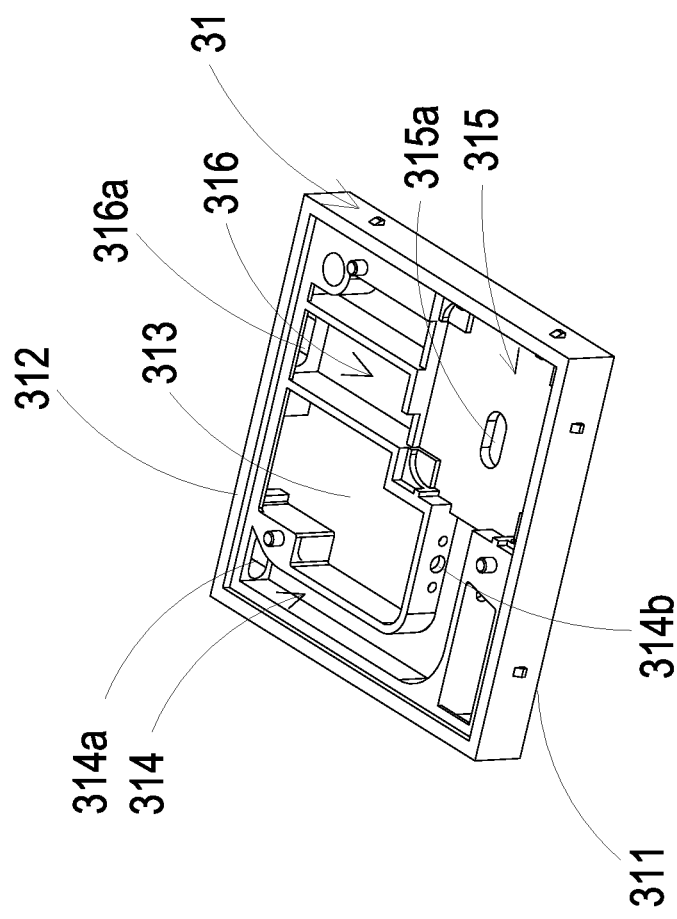
FIG. 3B is a schematic perspective view illustrating the base of the gas detection module of the present disclosure from another perspective angle.

In the embodiment, the driving circuit board 33 covers and is attached to the second surface 312 of the base 31 (as shown in FIG. 2C), and the laser component 34 is positioned and disposed on the driving circuit board 33, and is electrically connected to the driving circuit board 33. The particulate sensor 35 is positioned and disposed on the driving circuit board 33, and is electrically connected to the driving circuit board 33. The outer cover 36 covers the base 31 and is attached to the first surface 311 of the base 31. Moreover, the outer cover 36 includes a side plate 361. The side plate 361 includes an inlet opening 361a and an outlet opening 361b. When outer cover 36 covers the base 31, the inlet opening 361a is corresponding to the gas-inlet 314a of the base 31, and the outlet opening 361b is corresponding to the gas-outlet 316a of the base 31.

Figure 6A:
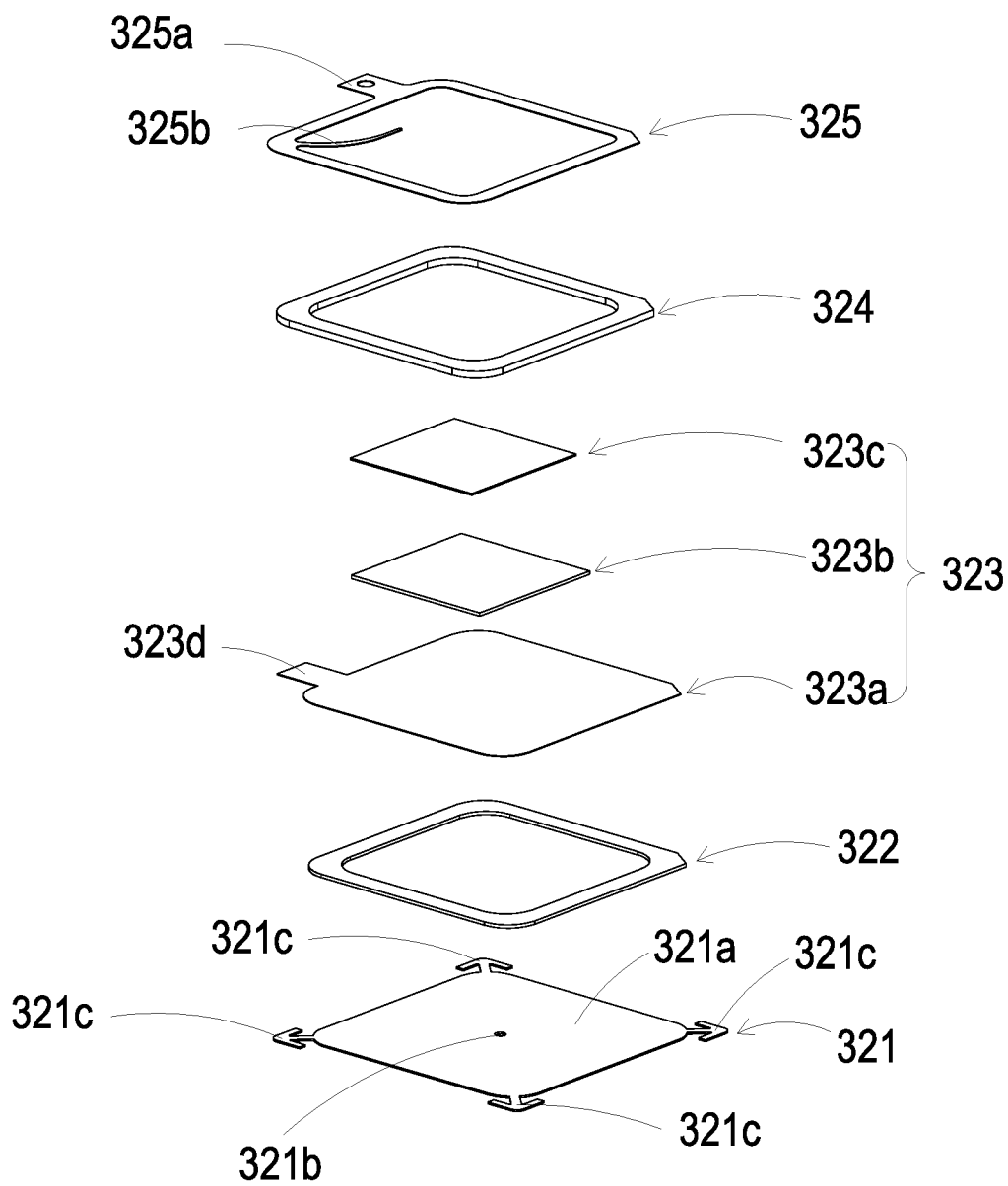
FIG. 6A is a schematic exploded view illustrating the piezoelectric actuator.
Figure 6B:
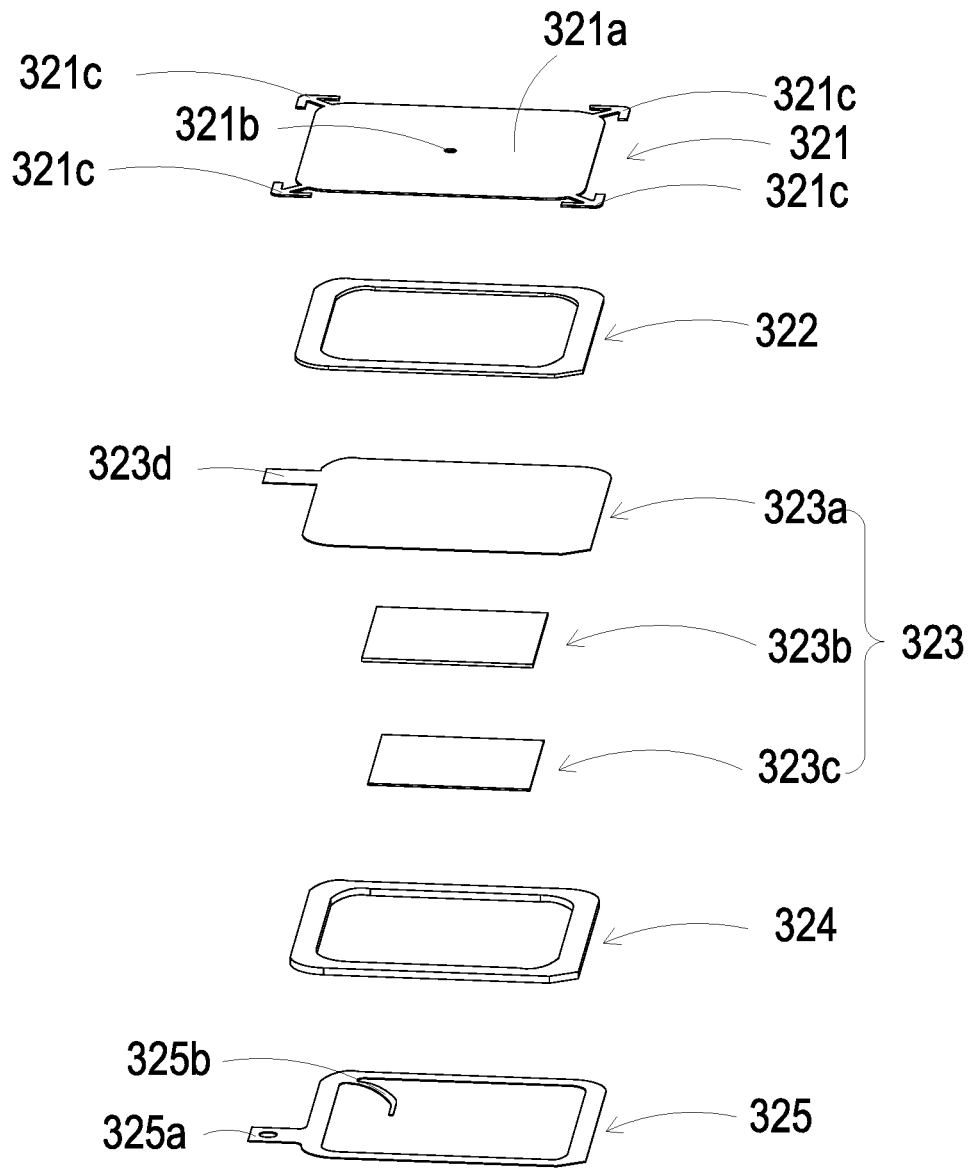
FIG. 6B is a schematic exploded view illustrating the piezoelectric actuator from another perspective angle.

Please refer to FIGS. 6A and 6B. In the embodiment, the piezoelectric actuator 32 includes a gas-injection plate 321, a chamber frame 322, an actuator element 323, an insulation frame 324 and a conductive frame 325.

In the embodiment, the gas-injection plate 321 is made by a flexible material and includes a suspension plate 321a, a hollow aperture 321b and a plurality of connecting elements 321c. The suspension plate 321a is a sheet structure and permitted to undergo a bending deformation. Preferably but not exclusively, the shape and the size of the suspension plate 321a are corresponding to an inner edge of the gas-guiding-component loading region 315. The shape of the suspension plate 321a is one selected from the group consisting of a square, a circle, an ellipse, a triangle and a polygon. The hollow aperture 321b passes through a center of the suspension plate 321a, so as to allow the gas to flow through. In the embodiment, there are four connecting elements 321c. Preferably but not exclusively, the number and the type of the connecting elements 321c mainly correspond to the positioning notches 315b of the gas-guiding-component loading region 315. Each connecting element 321c and the corresponding positioning notch 315b form an engagement structure, and are mutually engaged and fixed. Thus, the piezoelectric actuator 32 is disposed in the gas-guiding-component loading region 315.

The chamber frame 322 is carried and stacked on the gas-injection plate 321. In addition, the shape of the chamber frame 322 is corresponding to the gas-injection plate 321. The actuator element 323 is carried and stacked on the chamber frame 322. A resonance chamber 326 is collaboratively defined by the actuator element 323, the chamber frame 322 and the suspension plate 321a and formed among the actuator element 323, the chamber frame 322 and the suspension plate 321a. The insulation frame 324 is carried and stacked on the actuator element 323 and the appearance of the insulation frame 324 is similar to that of the chamber frame 322. The conductive frame 325 is carried and stacked on the insulation frame 324, and the appearance of the conductive frame 325 is similar to that of the insulation frame 324. In addition, the conductive frame 325 includes a conducting pin 325a and a conducting electrode 325b. The conducting pin 325a is extended outwardly from an outer edge of the conductive frame 325, and the conducting electrode 325b is extended inwardly from an inner edge of the conductive frame 325. Moreover, the actuator element 323 further includes a piezoelectric carrying plate 323a, an adjusting resonance plate 323b and a piezoelectric plate 323c. The piezoelectric carrying plate 323a is carried and stacked on the chamber frame 322. The adjusting resonance plate 323b is carried and stacked on the piezoelectric carrying plate 323a. The piezoelectric plate 323c is carried and stacked on the adjusting resonance plate 323b. The adjusting resonance plate 323b and the piezoelectric plate 323c are accommodated in the insulation frame 324. The conducting electrode 325b of the conductive frame 325 is electrically connected to the piezoelectric plate 323c. In the embodiment, the piezoelectric carrying plate 323a and the adjusting resonance plate 323b are made by a conductive material. The piezoelectric carrying plate 323a includes a piezoelectric pin 323d. The piezoelectric pin 323d and the conducting pin 325a are electrically connected to a driving circuit (not shown) of the driving circuit board 33, so as to receive a driving signal, such as a driving frequency and a driving voltage. In that, an electric circuit for the driving signal is formed by the piezoelectric pin 323d, the piezoelectric carrying plate 323a, the adjusting resonance plate 323b, the piezoelectric plate 323c, the conducting electrode 325b, the conductive frame 325 and the conducting pin 325a. Moreover, the insulation frame 324 is insulated between the conductive frame 325 and the actuator element 323, so as to avoid the occurrence of a short circuit. Thereby, the driving signal is transmitted to the piezoelectric plate 323c. After receiving the driving signal such as the driving frequency and the driving voltage, the piezoelectric plate 323c deforms due to the piezoelectric effect, and the piezoelectric carrying plate 323a and the adjusting resonance plate 323b are further driven to generate the bending deformation in the reciprocating manner.

As described above, the adjusting resonance plate 323b is located between the piezoelectric plate 323c and the piezoelectric carrying plate 323a and served as a buffer between the piezoelectric plate 323c and the piezoelectric carrying plate 323a. Thereby, the vibration frequency of the piezoelectric carrying plate 323a is adjustable. Basically, the thickness of the adjusting resonance plate 323b is greater than the thickness of the piezoelectric carrying plate 323a, and the thickness of the adjusting resonance plate 323b is adjustable, thereby adjusting the vibration frequency of the actuator element 323.

Figure 7A:
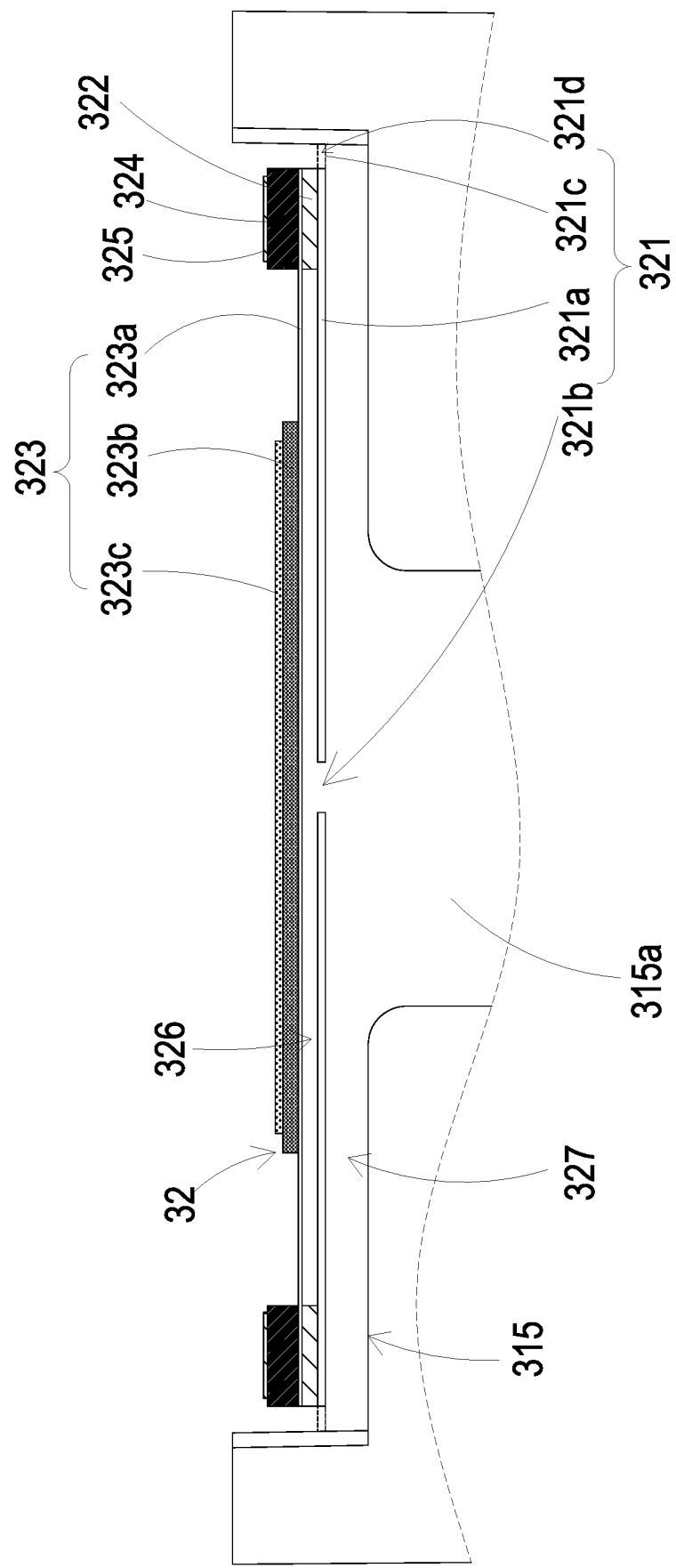
FIG. 7A is a schematic cross-sectional view illustrating the piezoelectric actuator accommodated in the gas-guiding-component loading region.

Please refer to FIG. 6A, FIG. 6B and FIG. 7A. In the embodiment, the plurality of connecting elements 321c are connected between the suspension plate 321a and an inner edge of the gas-guiding-component loading region 315 to define a plurality of clearances 321d for gas flowing.

Please refer to FIG. 7A. The gas-injection plate 321, the chamber frame 322, the actuator element 323, the insulation frame 324 and the conductive frame 325 are stacked and positioned in the gas-guiding-component loading region 315 sequentially. A flowing chamber 327 is formed between the gas-injection plate 321 and the bottom surface (not shown) of the gas-guiding-component loading region 315. The flowing chamber 327 is in fluid communication with the resonance chamber 326 between the actuator element 323, the chamber frame 322 and the suspension plate 321a through the hollow aperture 321b of the gas-injection plate 321. Through controlling the vibration frequency of the gas in the resonance chamber 326 and makes it close to the vibration frequency of the suspension plate 321a, the Helmholtz resonance effect is introduced between the resonance chamber 326 and the suspension plate 321a, and thereby improving the efficiency of gas transportation.

Figure 7B:
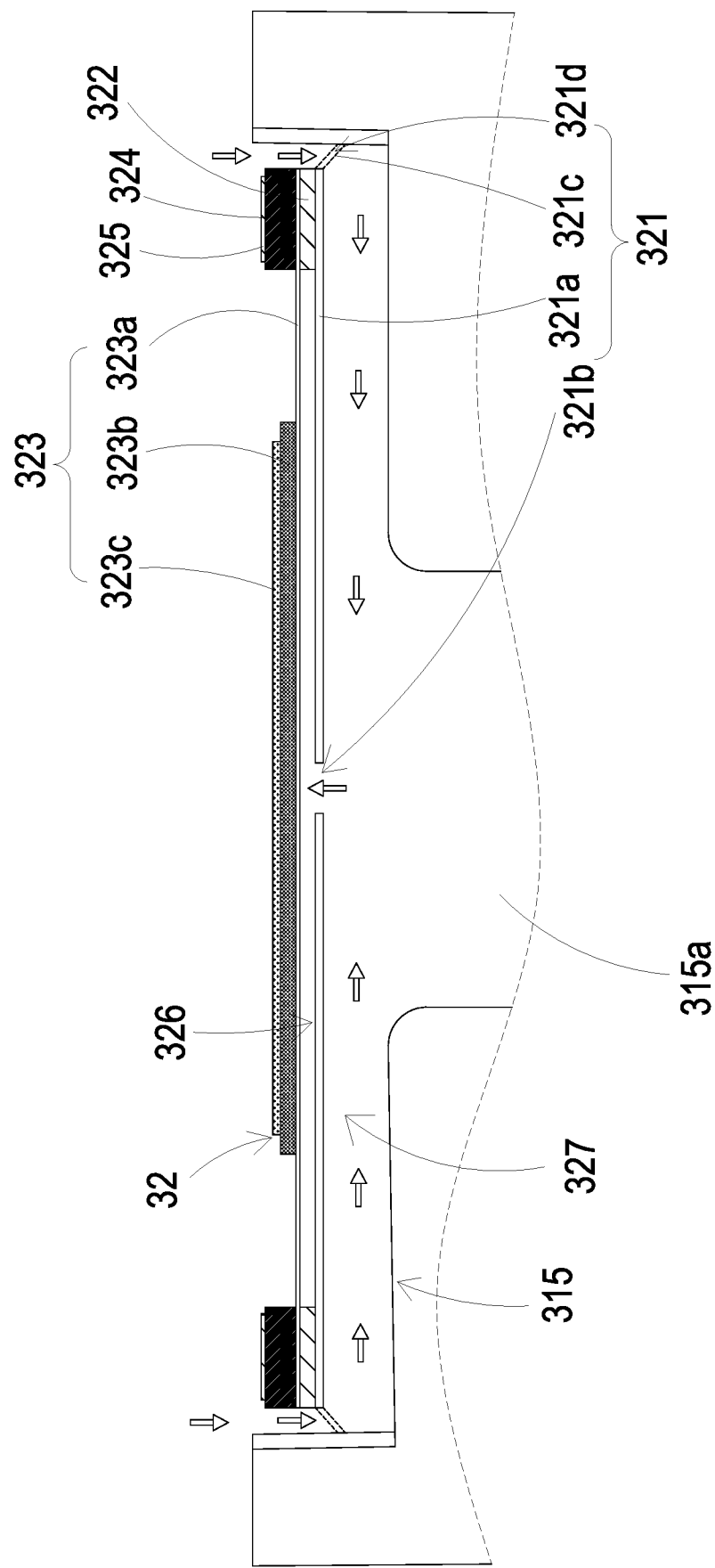
FIGS. 7B and 7C schematically illustrate the actions of the piezoelectric actuator of FIG. 7A.
Figure 7C:
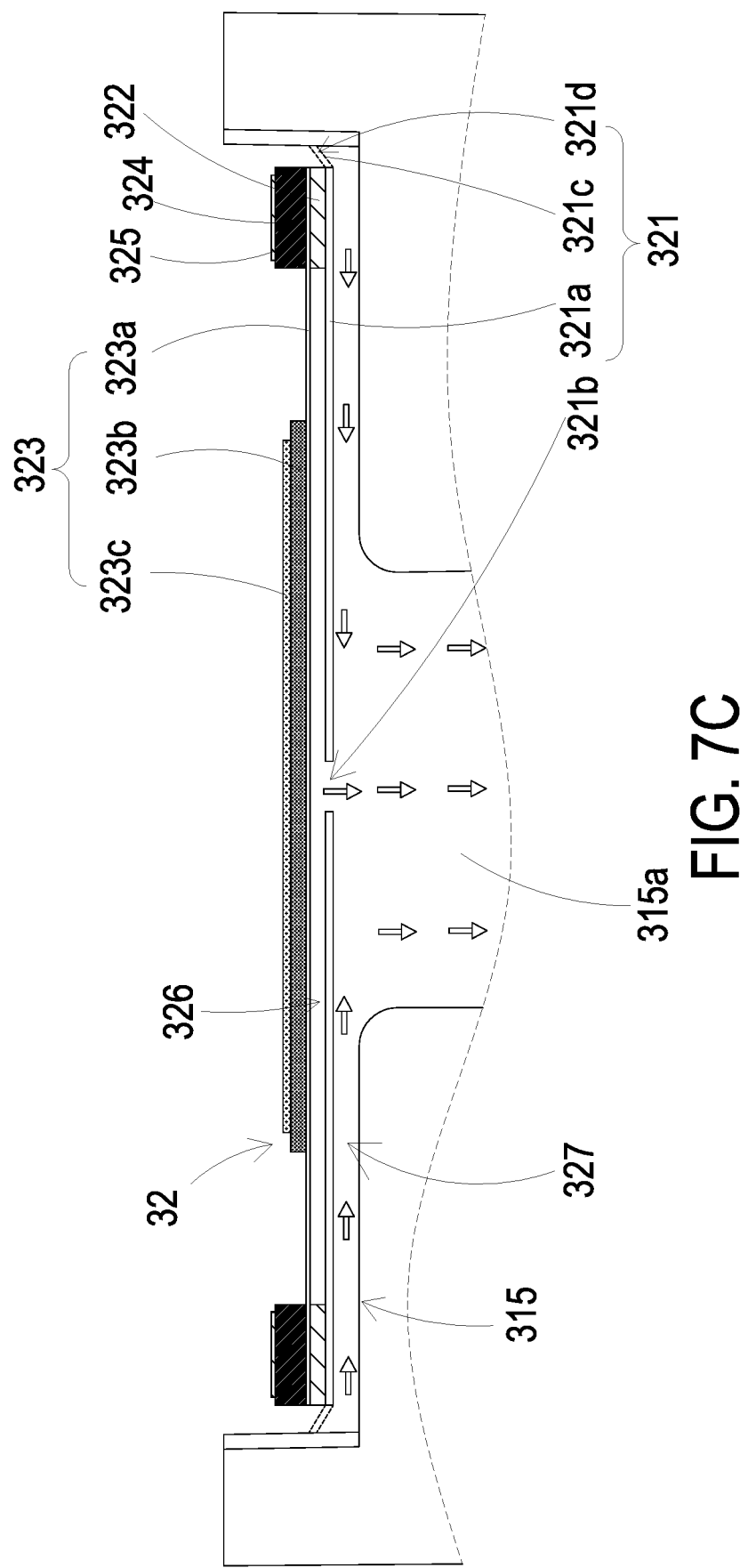

FIGS. 7B and 7C schematically illustrate the actions of the piezoelectric actuator of FIG. 7A. Please refer to FIG. 7B. When the piezoelectric plate 323c is moved away from the bottom surface of the gas-guiding-component loading region 315, the suspension plate 321a of the gas-injection plate 321 is moved away from the bottom surface of the gas-guiding-component loading region 315. In that, the volume of the flowing chamber 327 is expanded rapidly, the internal pressure of the flowing chamber 327 is decreased to form a negative pressure, and the gas outside the piezoelectric actuator 32 is inhaled through the clearances 321d and enters the resonance chamber 326 through the hollow aperture 321b. Consequently, the pressure in the resonance chamber 326 is increased to generate a pressure gradient. Further as shown in FIG. 7C, when the suspension plate 321a of the gas-injection plate 321 is driven by the piezoelectric plate 323c to move towards the bottom surface of the gas-guiding-component loading region 315, the gas in the resonance chamber 326 is discharged out rapidly through the hollow aperture 321b, and the gas in the flowing chamber 327 is compressed. In that, the converged gas is quickly and massively ejected out of the flowing chamber 327 in a gas state near to the ideal gas state of the Benulli's law. Moreover, according to the principle of inertia, the gas pressure inside the resonance chamber 326 after exhausting is lower than the equilibrium gas pressure outside, and the gas is introduced into the resonance chamber 326 again. By repeating the above actions shown in FIG. 7B and FIG. 7C, the piezoelectric plate 323c is driven to generate the bending deformation in a reciprocating manner. Moreover, the vibration frequency of the gas in the resonance chamber 326 is controlled to be close to the vibration frequency of the piezoelectric plate 323c, so as to generate the Helmholtz resonance effect and to achieve the gas transportation at high speed and in large quantities.

Figure 8A:
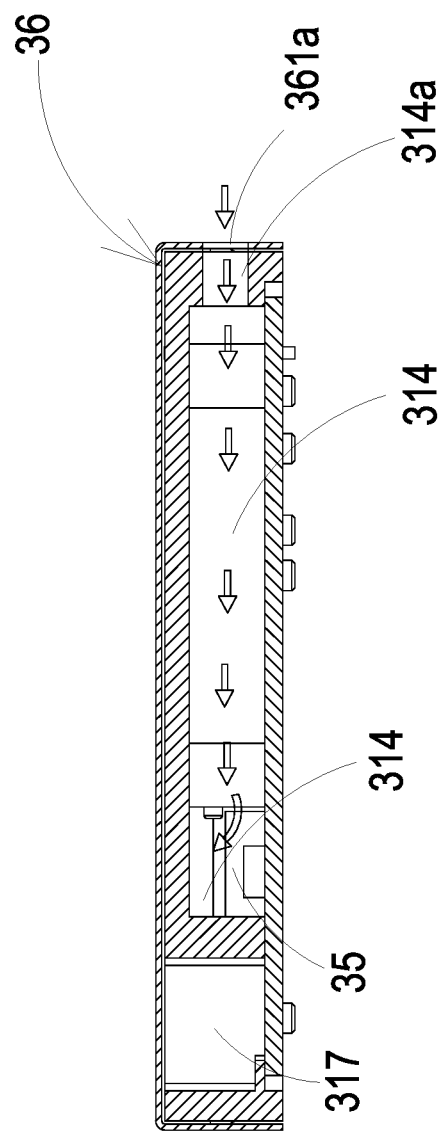
FIGS. 8A to 8C schematically illustrate gas flowing paths of the gas detection module.
Figure 8B:
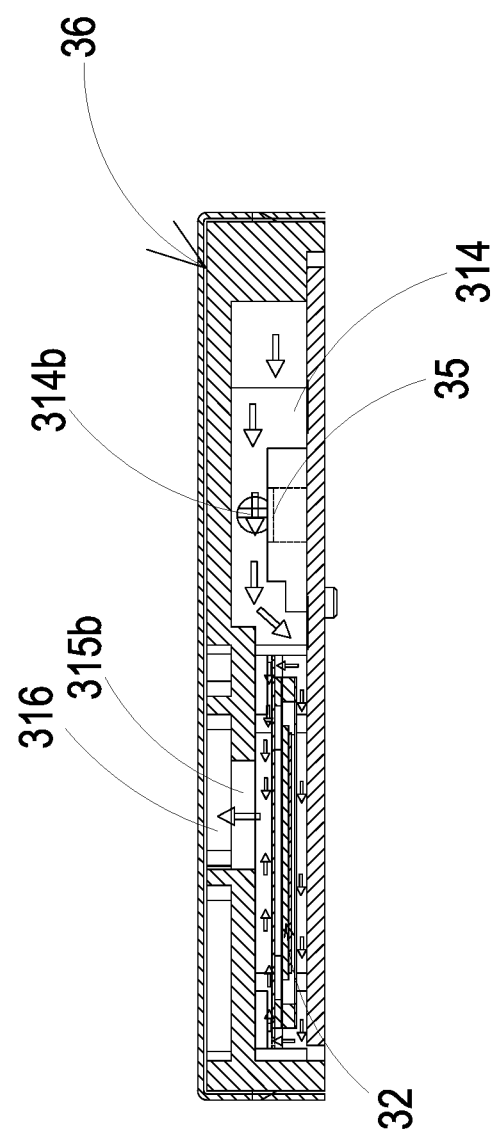
Figure 8C:
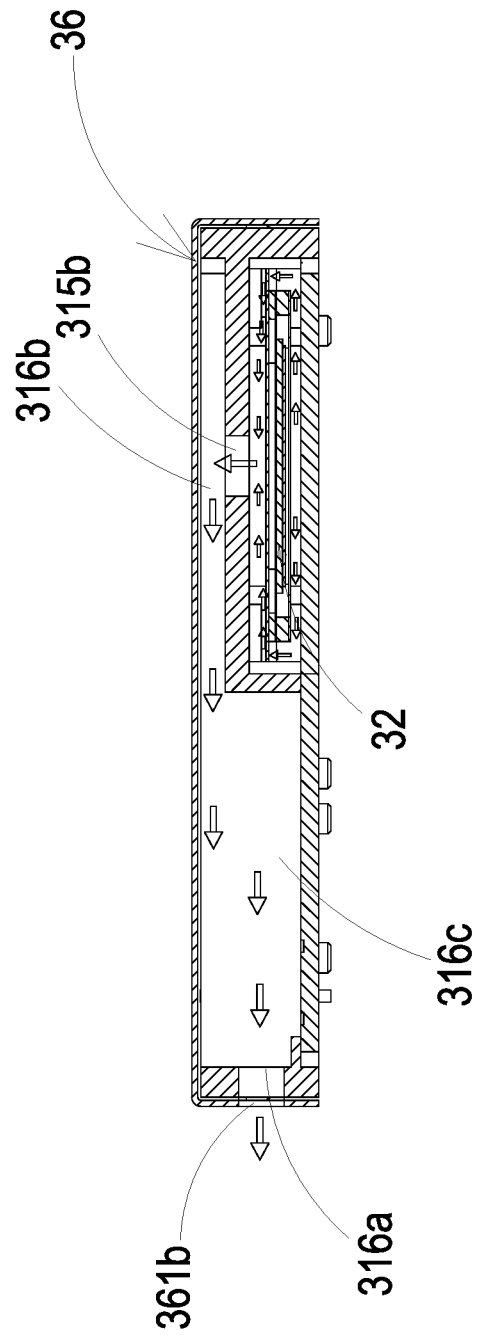

Please refer to FIGS. 8A to 8C. FIGS. 8A to 8C schematically illustrate gas flowing paths of the gas detection module 3. Firstly, as shown in FIG. 8A, the gas is inhaled through the inlet opening 361a of the outer cover 36, flows into the gas-inlet groove 314 of the base 31 through the gas-inlet 314a, and is transported to the position of the particulate sensor 35. Further as shown in FIG. 8B, the piezoelectric actuator 32 is enabled continuously to inhale the gas in the inlet path, so as to facilitate the gas to be introduced and transported above the particulate sensor 35 rapidly and stably. At this time, a projecting light beam emitted from the laser component 34 passes through the transparent window 314b to irritate the suspended particles contained in the gas flowing above the particulate sensor 35 in the gas-inlet groove 314. When the suspended particles contained in the gas are irradiated to generate scattered light spots, the scattered light spots are detected and calculated by the particulate sensor 35 for obtaining related information in regard to the sizes and the concentration of the suspended particles contained in the gas. Furthermore, the gas above the particulate sensor 35 is continuously driven and transported by the piezoelectric actuator 32, flowed into the ventilation hole 315a of the gas-guiding-component loading region 315, and transported to the first section 316b of the gas-outlet groove 316 (refers back to FIG. 3). As shown in FIG. 8C, after the gas flows into the first section 316b of the gas-outlet groove 316, the gas is continuously transported into the first section 316b by the piezoelectric actuator 32, and the gas in the first section 316b is pushed to the second section 316c. Finally, the gas is discharged out through the gas-outlet 316a and the outlet opening 361b.

Figure 9:
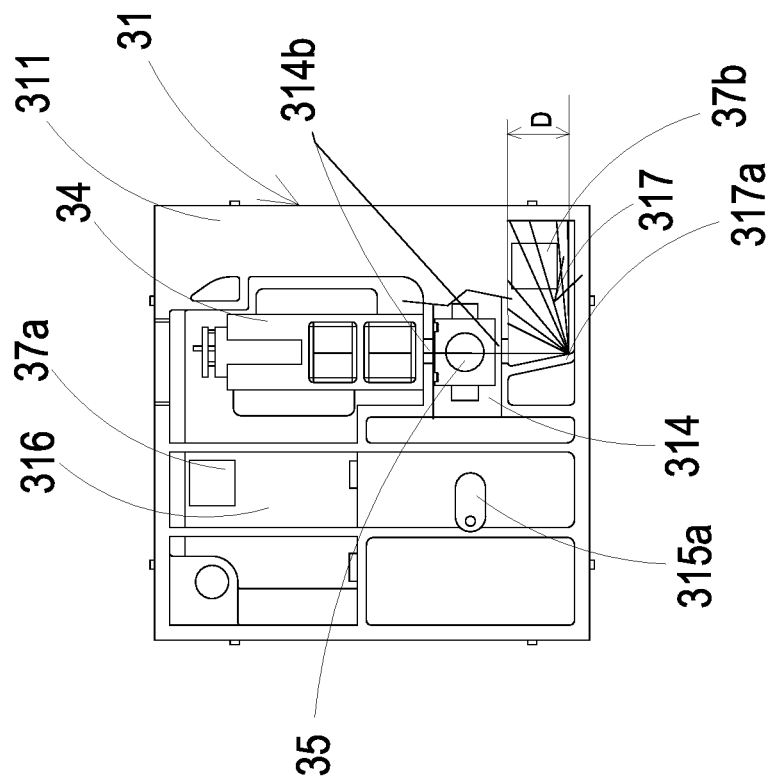
FIG. 9 schematically illustrates a light beam path emitted from the laser component.

As shown in FIG. 9, the base 31 further includes a light trapping region 317. The light trapping region 317 is hollowed out from the first surface 311 to the second surface 312 and is spatially corresponding to the laser loading region 313. In the embodiment, the light trapping region 317 is corresponding to the transparent window 314b so that the light beam emitted by the laser component 34 is projected into the light trapping region 317. The light trapping region 317 includes a light trapping structure 317a having an oblique cone surface. The light trapping structure 317a is spatially corresponding to the light beam path emitted from the laser component 34. In addition, the projecting light beam emitted from the laser component 34 is reflected into the light trapping region 317 through the oblique cone surface of the light trapping structure 317a. It prevents the projecting light beam from being reflected to the position of the particulate sensor 35. In the embodiment, a light trapping distance D is maintained between the transparent window 314b and a position where the light trapping structure 317a receives the projecting light beam. Preferably but not exclusively, the light trapping distance D is greater than 3 mm. When the light trapping distance D is less than 3 mm, the projecting light beam projected on the light trapping structure 317a could be easily reflected back to the position of the particulate sensor 35 directly due to excessive stray light generated after reflection, and resulted in distortion of detection accuracy.

Please refer to FIG. 2C and FIG. 9. The gas detection module 3 of the present disclosure can not only detect the suspended particles in the gas, but also detect the characteristics of the introduced gas. For example, the gas can be detected is one selected form the group consisting of formaldehyde, ammonia, carbon monoxide, carbon dioxide, oxygen and ozone. In the embodiment, the gas detection module 3 further includes a first volatile-organic-compound sensor 37a. The first volatile-organic-compound sensor 37a is positioned and disposed on the driving circuit board 33, electrically connected to the driving circuit board 33, and accommodated in the gas-outlet groove 316, so as to detect the gas flowing through the outlet path of the gas-outlet groove 316. Thus, the concentration or characteristics of volatile organic compounds contained in the gas in the outlet path is detected. In the embodiment, the gas detection module 3 further includes a second volatile-organic-compound sensor 37b. The second volatile-organic-compound sensor 37b is positioned and disposed on the driving circuit board 33, and electrically connected to the driving circuit board 33. In the embodiment, the second volatile-organic-compound sensor 37b is accommodated in the light trapping region 317. Thus, the concentration or characteristics of volatile organic compounds contained in the gas flowing through the inlet path of the gas-inlet groove 314 and transported into the light trapping region 317 through the transparent window 314b is detected.

Figure 10:
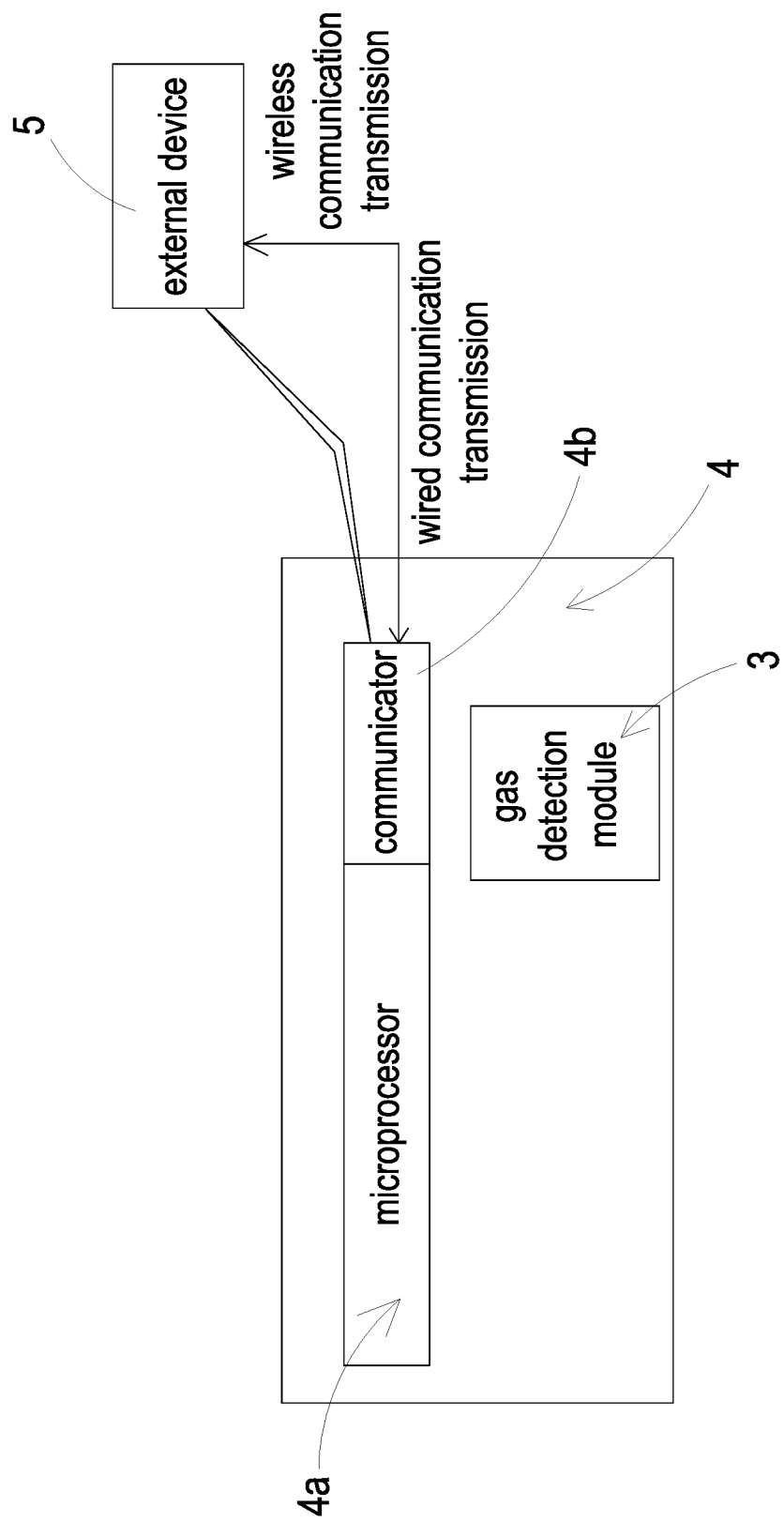
FIG. 10 is a block diagram showing the relationship between the controlling circuit unit and the related arrangement of the home device capable of gas detection according to the embodiment of the present disclosure.

Please refer to FIGS. 1 and 10 again. In the embodiment, the home device 100 further includes a controlling circuit unit 4. A microprocessor 4a and a communicator 4b are disposed on and electrically coupled with the controlling circuit unit 4. The gas detection module 3 is electrically connected to the controlling circuit unit 4. The microprocessor 4a can control the driving signal of the gas detection module 3, enable the gas detection module 3, and convert a detection raw data of the gas detection module 3 into a detection data for storing. In addition, the microprocessor 4a can control the driving signal of the piezoelectric actuator 32 and enables the piezoelectric actuator 32, and controls the operation of the home device 100 according to the detection data. Thereby, the piezoelectric actuator 32 is automatically enabled and the air volume thereof is automatically controlled and adjusted. The communicator 4b can receive the detection data outputted from the microprocessor 4a and externally transmit the detection data to an external device 5 through the communication transmission for storing, such that allowing the external device 5 to generate a gas detection information and an alarm. Preferably but not exclusively, the above-mentioned external device 5 is one selected from the group consisting of a cloud system, a portable device and a computer system. Preferably but not exclusively, the communication transmission is the wired communication transmission, such as USB connection transmission. Preferably but not exclusively, the communication transmission is the wireless communication transmission, such as Wi-Fi transmission, Bluetooth transmission, a radio frequency identification transmission or a near field communication transmission.

From the above descriptions, the present disclosure provides a home device. Through combining the gas detection module with the home device, the home device of present invention can monitor the gas information surrounding the user for allowing the user to obtain the air quality in the surrounding environment. The environment information can be provided immediately to warn the user in the environment, so as to avoid the harm and facilitate the user to away from the hazard environment immediately. The present disclosure includes the industrial applicability.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims which are to be accorded with the broadest interpretation so as to encompass all such modifications and similar structures.

What is claimed is:

1. A home device capable of gas detection, comprising:
a main body having at least one inlet, at least one outlet and a gas flowing channel disposed between the at least one inlet and the at least one outlet; and
a gas detection module, disposed in the gas flowing channel of the main body, comprising a base, a gas-inlet groove, a driving circuit board, an outer cover, a piezoelectric actuator and at least one sensor, wherein gas is inhaled into the gas flowing channel through the inlet, transported to the at least one sensor to be detected, and discharged out through the outlet by the piezoelectric actuator, so as to obtain gas information,
wherein the outer cover is attached to a first surface of the base, the driving circuit board is attached to a second surface of the base,
wherein the gas detection module includes a gas flowing path comprising a gas-inlet groove recessed from the second surface and on an upstream side of the at least one sensor, a gas-guiding-component loading region recessed from the second surface, opposite to the first surface, and on a downstream side of the at least one sensor, and a gas-outlet groove recessed from the first surface and on a downstream side of the gas-guiding-component loading region, and
wherein the gas flowing path is configured in such a manner that the gas passes the gas-inlet groove and the gas-outlet groove respectively in a direction parallel with the first and second surfaces.

2. The home device capable of gas detection according to claim 1, wherein the home device is a video and audio output device and is one selected from a group consisting of a player, a radio, a robot, a stereo, a clock, a wall clock, a pair of walkie-talkies, a printer, a projector, a Bluetooth speaker and a smart speaker.

3. The home device capable of gas detection according to claim 1, wherein the home device is an environmental electrical appliance and is one selected from a group consisting of an air purifier, an air cleaner, a humidifier, a plant detector, an air detector, an air conditioner socket, an electric heater, an air conditioner, a fan, a temperature controller, a dehumidifier and an anion air purifier.

4. The home device capable of gas detection according to claim 1, wherein the home device is a household appliance and is one selected from a group consisting of a toilet, a washing machine, a mosquito killer lamp, a sweeping robot, a water heater, a drying rack, a floor mopping machine, a water dispenser, a smart electric lift table, an electric blanket, a vacuum cleaner, a clothes dryer machine, a towel heater rack, a temperature and humidity measuring device and an automatic temperature controller.

5. The home device capable of gas detection according to claim 1, wherein the home device is a kitchen appliance and is one selected from a group consisting of a refrigerator, a microwave oven, an electric kettle, a water purifier, a coffee machine, a milk frother, an electric cooker, a range hood, an induction cooker, a pressure cooker, a dishwasher, a juicer, a steaming oven, a sink, a hard water softener, a smoke sensor, a gas sensor and a water sensor.

6. The home device capable of gas detection according to claim 1, wherein the home device is a home security device and is one selected from a group consisting of a door lock, a video doorbell, a safe and a window opener.

7. The home device capable of gas detection according to claim 1, wherein the home device is a lighting device and is one selected from a group consisting of a ceiling lamp, a bedside lamp, a table lamp, a light bulb and a fan lamp.

8. The home device capable of gas detection according to claim 1, wherein the home device is a power conversion device and is one selected from a group consisting of a socket, a power strip and a switch.

9. The home device capable of gas detection according to claim 1, wherein the home device is a camera security equipment and is one selected from a group consisting of a camera and a camcorder.

10. The home device capable of gas detection according to claim 1, wherein the home device is a wearable device and is one selected from a group consisting of a smart mask, a smart clothing, a smart textile, a smart belt, a smart necklace, a smart brooch and a bracelet.

11. The home device capable of gas detection according to claim 1, wherein the home device is a baby product and is one selected from a group consisting of a baby monitor, a stroller and a crib.

12. The home device capable of gas detection according to claim 1, wherein the at least one sensor of the gas detection module comprises a particulate sensor, and the gas detection module further comprises:
the base comprising:
the first surface;
the second surface opposite to the first surface;
a laser loading region hollowed out from the first surface to the second surface;
the gas-inlet groove concavely formed from the second surface and disposed adjacent to the laser loading region, wherein the gas-inlet groove comprises a gas-inlet and two lateral walls, the gas-inlet is in communication with an environment outside the base, and a transparent window is opened on the lateral wall and is in communication with the laser loading region;

the gas-guiding-component loading region concavely formed from the second surface and in communication with the gas-inlet groove, wherein a ventilation hole penetrates a bottom surface of the gas-guiding-component loading region; and the gas-outlet groove concavely formed from the first surface, spatially corresponding to the bottom surface of the gas-guiding-component loading region, and hollowed out from the first surface to the second surface in a region where the first surface is not aligned with the gas-guiding-component loading region, wherein the gas-outlet groove is in communication with the ventilation hole, and a gas-outlet is disposed in the gas-outlet groove and in communication with the environment outside the base;

the driving circuit board covering the second surface of the base;

and the laser component is positioned and disposed on the driving circuit board, electrically connected to the driving circuit board, and accommodated in the laser loading region, wherein a light beam path emitted from the laser component passes through the transparent window and extends in a direction perpendicular to the gas-inlet groove;

the outer cover covering the first surface of the base and comprising a side plate, wherein the side plate has an inlet opening spatially corresponding to the gas-inlet and an outlet opening spatially corresponding to the gas-outlet, respectively, wherein the piezoelectric actuator accommodated in the gas-guiding-component loading region, wherein the particulate sensor is positioned and disposed on the driving circuit board, electrically connected to the driving circuit board, and is disposed in the gas-inlet groove at an position orthogonal to the light beam path of the laser component, so as to detect suspended particles passing through the gas-inlet groove and irradiated by a projecting light beam emitted from the laser component, wherein the first surface of the base is covered with the outer cover, and the second surface of the base is covered with the driving circuit board, so that an inlet path is defined by the gas-inlet groove, and an outlet path is defined by the gas-outlet groove, thereby the gas is inhaled from the environment outside the base, transported into the inlet path through the inlet opening, passed through the particulate sensor to detect the concentration of the suspended particles contained in the gas, transported out of the outlet path through the ventilation hole, and then discharged through the outlet opening by the piezoelectric actuator.

13. The home device capable of gas detection according to claim 12, wherein the base comprises a light trapping region hollowed out from the first surface to the second surface and spatially corresponding to the laser loading region, wherein the light trapping region comprises a light trapping structure having an oblique cone surface spatially corresponding to the light beam path.

14. The home device capable of gas detection according to claim 13, wherein a light trapping distance is maintained between the transparent window and a position where the light trapping structure receives the projecting light beam, and the light trapping distance is greater than 3 mm.

15. The home device capable of gas detection according to claim 13, wherein the at least one sensor of the gas detection module comprises a second volatile-organic-compound sensor positioned and disposed on the driving circuit board, electrically connected to the driving circuit board, and accommodated in the light trapping region, so as to detect the gas flowing through the inlet path of the gas-inlet groove and transported into the light trapping region through the transparent window.

16. The home device capable of gas detection according to claim 12, wherein the particulate sensor is a PM2.5 sensor.

17. The home device capable of gas detection according to claim 12, wherein the piezoelectric actuator comprises:

a gas-injection plate comprising a plurality of connecting elements, a suspension plate and a hollow aperture, wherein the suspension plate is permitted to undergo a bending deformation, the plurality of connecting elements are adjacent to a periphery of the suspension plate, and the hollow aperture is formed at a center of the suspension plate, wherein the suspension plate is fixed through the plurality of connecting elements, and the plurality of connecting elements are configured for elastically supporting the suspension plate, wherein a flowing chamber is formed between the gas-injection plate and the bottom surface of the gas-guiding-component loading region, and at least one clearance is formed among the plurality of connecting components and the suspension plate;

a chamber frame carried and stacked on the suspension plate;

an actuator element, carried and stacked on the chamber frame for being driven in response to an applied voltage to undergo the bending deformation in a reciprocating manner, comprising:

a piezoelectric carrying plate carried and stacked on the chamber frame;

an adjusting resonance plate carried and stacked on the piezoelectric carrying plate; and a piezoelectric plate carried and stacked on the adjusting resonance plate, wherein the piezoelectric plate is configured to drive the piezoelectric carrying plate and the adjusting resonance plate to generate the bending deformation in the reciprocating manner by the applied voltage;

an insulation frame carried and stacked on the actuator element; and a conductive frame carried and stacked on the insulation frame, wherein a resonance chamber is formed between the actuator element, the chamber frame and the suspension plate, wherein when the actuator element is enabled to drive the gas-injection plate to move and result in resonance, the suspension plate of the gas-injection plate is driven to generate the bending deformation in a reciprocating manner, the gas is inhaled through the clearance, flowed into the flowing chamber, and discharged out, so as to achieve gas transportation.

18. The home device capable of gas detection according to claim 12, wherein the at least one sensor of the gas detection module comprises a first volatile-organic-compound sensor positioned and disposed on the driving circuit board, electrically connected to the driving circuit board, and accommodated in the gas-outlet groove, so as to detect the gas flowing through the outlet path of the gas-outlet groove.

19. The home device capable of gas detection according to claim 1, further comprising a controlling circuit unit, wherein a microprocessor and a communicator are disposed on and electrically coupled with the controlling circuit unit, and the gas detection module is electrically connected to the controlling circuit unit, wherein the microprocessor enables the gas detection module to detect and operate by controlling a driving signal of the gas detection module, and converts a detection raw data of the gas detection module into a detection data for storing, wherein the communicator receives the detection data outputted by the microprocessor, and allows the detection data to be externally transmitted to an external device through the communication transmission for storing, thereby the external device generates a gas detection information and an alarm.

20. The home device capable of gas detection according to claim 19, wherein the external device is one selected from the group consisting of a cloud system, a portable device and a computer system.

* * * * *